US012605334B2

(12) United States Patent
Sarkas

(10) Patent No.: US 12,605,334 B2
(45) Date of Patent: *Apr. 21, 2026

---

(54) METHOD OF ENHANCING THE EFFICACY AND STABILITY OF INGREDIENTS IN SUSPENSIONS

(71) Applicant: Nanophase Technologies Corporation, Romeoville, IL (US)

(72) Inventor: Harry W. Sarkas, Shorewood, IL (US)

(73) Assignee: Solésence, Inc., Romeoville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,416

(22) Filed: Dec. 4, 2023

(65) Prior Publication Data

US 2024/0293313 A1 Sep. 5, 2024

Related U.S. Application Data

(63) Continuation of application No. 17/489,071, filed on Sep. 29, 2021, now abandoned, which is a continuation of application No. 16/537,337, filed on Aug. 9, 2019, now Pat. No. 11,154,501.

(51) Int. Cl.
*A61K 9/10* (2006.01)
*A61K 9/16* (2006.01)
*A61K 31/4166* (2006.01)

(52) U.S. Cl.
CPC .............. *A61K 9/10* (2013.01); *A61K 9/1682* (2013.01); *A61K 31/4166* (2013.01)

(58) Field of Classification Search
CPC .......... A61K 9/10; A61K 8/044; A61K 31/12; A61K 8/35
See application file for complete search history.

(56) References Cited

U.S. PATENT DOCUMENTS

| | | | |
|---|---|---|---|
| 3,043,745 A | 7/1962 | Singer | |
| 9,095,574 B2 | 8/2015 | Farber | |
| 11,154,501 B2 * | 10/2021 | Sarkas | ............... A61K 31/4166 |
| 2006/0118000 A1 | 6/2006 | Isager | |
| 2013/0011347 A1 * | 1/2013 | Tanner | ................... A61K 8/678 |
| | | | 424/59 |
| 2021/0038518 A1 | 2/2021 | Sarkas | |

FOREIGN PATENT DOCUMENTS

| | | |
|---|---|---|
| EP | 0380157 | 1/1990 |
| KR | 101894521 | 9/2018 |

| | | | |
|---|---|---|---|
| WO | 2010/144812 | | 12/2010 |
| WO | 2020/175703 | | 9/2020 |
| WO | WO-2020175703 A1 * | 9/2020 |

OTHER PUBLICATIONS

English machine translation of WO-2020175703-A1 made May 30, 2023. (Year: 2023).*
Akema Fine Chemicals, "Allantoin CTFA", Akema srl, Product Information, pp. 1-2, found at www.akema.it/pdf/ALLANTOIN. pdf, (2008).
Making Cosmetics, "Allantoin", Specification Sheet, 2 pages, (2018).
Akema Fine Chemicals, "Allantoin, a safe and effective skin protectant", Akema srl, 13 pages, (2006).
Becker, L.C. et al., "Final report of the safety assessment of allantoin and its related complexes", International Journal of Toxicology, vol. 29, supplement 2, pp. 84s-97s, (2010).
Igile, G.O. et al., "Rapid method for the identification and quantification of Allantoin in body creams and lotions for regulatory activities", International Journal of Current Microbiology and Applied Sciences, vol. 3, No. 7, pp. 552-557, (2014).
Van Westen, T. et al., "Effect of temperature cycling on ostwald ripening", Crystal Growth & Design, vol. 18, pp. 4952-4962, (2018).
Bowen, P., "Particle size distribution measurement from millimeters to nanometers and from rods to platelets", Journal of Dispersion Science and Technology, vol. 23, No. 5, pp. 631-662, (2002).
International Search Report and Written Opinion dated Oct. 14, 2020 for PCT application No. PCT/US2020/045479, pp. 1-15.
Savjani, K.T. et al., "Drug solubility: Importance and enhancement techniques", International Scholarly Research Network, ISRN Pharmaceutics, vol. 2012, pp. 1-10, (2012).
Kalepu, S. et al., "Insoluble drug delivery strategies: review of recent advances and business prospects", Acta Pharmaceutica Sinica B, vol. 5, No. 5, pp. 442-453, (2015).
Common Technical Document (CTD) Question and Answer Book, Ministry of Food and Drug Safety, Republic of Korea, (Dec. 31, 2015).
Guidelines on Stability Testing of Cosmetic Products, Ministry of Food and Drug Safety, Republic of Korea, (Dec. 16, 2010).
ICH Harmonised Tripartite Guideline, "Stability testing of new drug substances and products Q1A(R2)", International Conference on Harmonisation of Technical Requirements for Registration of Pharmaceuticals for human use, 24 pages, Feb. 6, 2003.
Ferrington, D.G. et al., "Human tactile detection thresholds: modification by inputs from specific tactile receptor classes", The Journal of Physiology, vol. 272, No. 2, pp. 415-433, (1977).

* cited by examiner

*Primary Examiner* — Michael B. Pallay
(74) *Attorney, Agent, or Firm* — EVAN LAW GROUP LLC

(57) ABSTRACT

A composition comprises a low-solubility ingredient having a particle size of at most 10 μm dispersed in a solvent. The ingredient is present in an amount greater than the saturation limit of the ingredient in the solvent. The composition passes the freeze-thaw cycling test.

20 Claims, 6 Drawing Sheets

10.0% ALLANTOIN

MILLED          MOSTLY DISSOLVED 1.52% ALLANTOIN

DISSOLVED          MILLED

MILLED                    MOSTLY DISSOLVED 10.0% ALLANTOIN 1.52% ALLANTOIN

MILLED                    DISSOLVED

FROM DISSOLVED 1.52%
40X

FROM DISSOLVED 1.52%
200X

FROM MILLED 1.52%
40X

FROM MILLED 1.52%
200X

METHOD OF ENHANCING THE EFFICACY AND STABILITY OF INGREDIENTS IN SUSPENSIONS

BACKGROUND

Products intended for human or animal use, such as those regulated under the U.S. Federal Food, Drug, and Cosmetic Act, often include a combination of ingredients that are classified by the U.S. Food and Drug Administration (FDA) as monographed drugs (known as active ingredients or "drug actives") as well as ingredients that provide recognized beneficial effects but are not classified by the FDA as monographed drugs (known as inactive ingredients or "claims actives"). These products are typically formulated as solutions to deliver effective amounts of the drug actives and claims actives to the target sites.

Formulating solutions can significantly complicate the manufacturing process since many drug actives and claims actives have poor or limited solubility in liquid delivery vehicles under ambient and human topical use temperatures. In addition, some drug actives and claims actives are only soluble in solvents that are unsuitable for human topical use. For example, skin care ingredients such as antioxidants, skin soothing agents, skin brightening agents and vitamins are only soluble at meaningful levels in solvents such as acetone, dichloromethane, dimethyl sulfoxide and tetrahydrofuran.

Manufacturers can improve the solubility of drug actives and claims actives in solvents by dissolving these ingredients at elevated temperatures to ensure complete dissolution. Solution preparation at elevated temperatures requires manufacturers to account for the concentration limit of drug actives and claims actives in solution. For example, adding a claims active ingredient to an elevated temperature solution in an amount below its concentration limit at ambient temperature may impose a concentration limit that is below the level necessary for efficacy, which will prevent the claims active from providing the desired effect in the final product. In addition, it is common for drug actives and claims actives to have a minimum effective concentration that is above the ambient concentration limit. This situation requires manufacturers to formulate supersaturated solutions to deliver an effective amount of the drug actives and claims actives.

Supersaturated solutions are problematic since they are unstable and may experience uncontrolled precipitation of the drug actives and claims actives. The precipitation of ingredients often results in the formation of large, macroscopic crystals. Products containing visible crystals are aesthetically unacceptable to consumers and will reduce sales of the finished products. Larger crystals are a significant problem because they can be felt by the consumer during application. Crystals larger than 10 μm are perceived as grit by consumers, while crystals larger than 100 μm are perceived as "glass shards" and can be highly irritating when applied.

The precipitation of drug actives and claims actives is also problematic because it reduces the efficacy of the finished product. Larger crystals can physically prevent ingredients in formulations from being delivered to the target site. For example, in ultraviolet (UV) light protective formulations such as sunscreens, crystals that have precipitated out of solution will physically prevent the drug actives that provide UV protection from being distributed to the skin. This results in a phenomenon known as "break through burn" and can cause erythema or sunburn at the areas of the skin without adequate UV protection.

A number of other conditions can result in precipitation of formulation ingredients. Precipitation of ingredients can occur when aqueous-borne ingredients in a formulation have poor solubility at physiological pH ranges but enhanced solubility outside of physiological pH ranges. In addition, temperature fluctuations during storage and transport, such as freeze-thaw conditions, can result in precipitation of ingredients in formulations and large crystal formation.

Certain drug actives and claims actives are particularly susceptible to precipitation out of formulations because their solubilities force manufacturers to form supersaturated solutions during their preparation. A well-known example of an ingredient that is prone to precipitate out of formulations is allantoin (also known as (2,5-dioxo-4-imidazolidinyl) urea, 5-ureidohydantoin or glyoxyldiureide), which is used in a wide variety of products for its skin conditioning, moisturizing, skin soothing, wound healing, keratolytic, skin softening/smoothing, anti-inflammatory and anti-irritant properties (Igile, G. O. et al., "Rapid method for the identification and quantification of allantoin in body creams and lotions for regulatory activities", International Journal of Current Microbiology and Applied Sciences, Vol. 3. No. 7, pp. 552-557 (2014)). The FDA has approved the use of allantoin as a skin protectant when present in formulations in an amount of 0.5-2% (21 CFR 347.10(a)). However, allantoin has a solubility limit of 0.5% in water at 25° C., which prevents manufacturers from preparing formulations including allantoin as a skin protectant across the full range of concentrations specified in the FDA monograph. The limited solubility of allantoin forces manufacturers to choose between using less allantoin than allowed by the FDA or creating products that are prone to stability issues that can impair their efficacy.

Other ingredients that are known to experience precipitation issues include quercetin, quercetin dihydrate, rutin, multifunctional curcuminoid additives and their derivatives (including curcumin, demethoxycurcumin, bisdemethoxycurcumin and tetrahydrodiferuloyl-methane), phenol antioxidants (including polyphenols such as tannic acid, ellagic acid and raspberry ellagitannin), flavonoids, isoflavonoids such as galbridin, flavanols (including catechins such as epigallocatechin gallate (EGCG)), dimethylmethoxy chromanol and carotenoids (including xanthophylls, astaxanthin, zeaxanthin and lutein).

SUMMARY

In a first aspect, the invention is a composition comprising a low-solubility ingredient having a particle size of at most 10 μm dispersed in a solvent. The ingredient is present in an amount greater than the saturation limit of the ingredient in the solvent. The composition passes the freeze-thaw cycling test.

In a second aspect, the invention is a method of preparing a suspension comprising reducing the particle size of a low-solubility ingredient to at most 10 μm, and adding the ingredient to a solvent. The ingredient is present in an amount greater than the saturation limit of the ingredient in the solvent. The suspension passes the freeze-thaw cycling test.

In a third aspect, the invention is allantoin having an average particle size of at most 10 μm.

Definitions

The term "particle size" means the average diameter of the particle as viewed by optical microscopy, electron microscopy or determined by static light scattering, unless otherwise stated. Particle size may be expressed by number or by volume, or as a number weighted or volume weighted distribution.

The term "low-solubility" means an ingredient that has a solubility limit of at most 2.0% in a given solvent at 25° C.

The term "suspension" means a composition that includes undissolved particles.

The "freeze-thaw cycling test" is a test of the stability of at least one ingredient dispersed in a solvent. First, a test composition is prepared by adding the at least one ingredient to the solvent. Next, the test composition is placed in a freezer at −20° C. After six hours the test composition is removed from the freezer and allowed to return to room temperature (25° C.). The test composition is then visually analyzed by observation with the naked eye and by viewing a sample of the test composition using an optical microscope at 40×-200× magnification. The test composition is considered to pass the freeze-thaw cycling test if no crystals are discernable by eye and if the test composition contains no particles larger than 10 microns (10 μm) in at least one aspect when viewed under optical microscopy.

The "extended freeze-thaw cycling test" is a test of the stability of at least one ingredient dispersed in a solvent. First, a test composition is prepared by adding the at least one ingredient to the solvent. Next, the test composition is placed in a freezer at −20° C. After six hours the test composition is removed from the freezer and allowed to return to room temperature (25° C.). The test composition is placed in the freezer at −20° C. for six hours and allowed to return to room temperature an additional nine times. The test composition is then visually analyzed by observation with the naked eye and by viewing a sample of the test composition using an optical microscope at 40×-200× magnification. The test composition is considered to pass the extended freeze-thaw cycling test if no crystals are discernable by eye and if the test composition contains no particles larger than 10 microns (10 μm) in at least one aspect when viewed under optical microscopy.

The "shelf stability test" is a test of the long-term stability of a composition containing at least one ingredient dispersed in a solvent. First, a test composition is prepared by adding the at least one ingredient to the solvent. Next, the test composition is placed in a controlled environment at 25° C. After 18 months the test composition is removed from the controlled environment. The test composition is then visually analyzed by observation with the naked eye and by viewing a sample of the composition using an optical microscope at 40×-200× magnification. The test composition is considered to pass the shelf stability test if no crystals are discernable by eye and if the test composition contains no particles larger than 10 microns (10 μm) in at least one aspect when viewed under optical microscopy.

The "skin feel test" is a test of the suitability of a composition containing at least one ingredient dispersed in a solvent for topical use. First, a test composition is prepared by adding the at least one ingredient to the solvent. Next, the test composition is applied to the skin of a human tester. The test composition is considered to pass the skin feel test if the human tester does not perceive any solids or grit after applying the test composition to his or her skin.

All percentages (%) are weight/weight percentages, unless stated otherwise.

BRIEF DESCRIPTION OF THE DRAWINGS

The invention can be better understood with reference to the following drawings and description.

DETAILED DESCRIPTION

Figure 1:
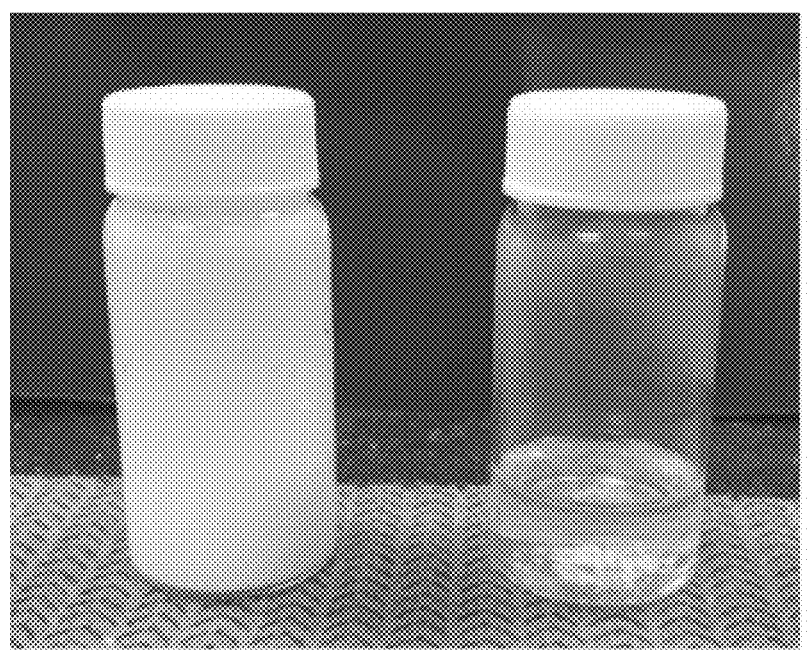
FIG. 1 is a photograph of a 10.0 wt % allantoin suspension prepared by reducing the particle size of allantoin and a 10.0 wt % allantoin solution prepared without reducing the particle size of allantoin.

Manufacturers have attempted various changes to existing manufacturing processes to reduce or prevent the precipitation of drug actives and claims actives from formulations. Modifications to the delivery system include the use of porous delivery systems and liposomal delivery systems. These modifications are typically costly and highly complex. In addition, the use of a different delivery system often still results in formulations in which the drug actives and claims actives are concentration limited Manufacturers have also attempted to chemically modify formulation ingredients to improve their stability. Chemical modifications to the drug actives or claims actives include forming chemical derivatives of these ingredients. However, derivatization often compromises efficacy. For example, the functional groups available for derivatization in antioxidants are typically the same functional groups that impart efficacy, and the formation of multiple derivatives has been shown to drastically reduce or even eliminate the antioxidant power.

It has been recognized that low-solubility drug actives and claims actives in suspensions exhibit crystal growth through Ostwald ripening. Ostwald ripening is a slow, thermodynamically-driven natural process in which small particles in solution dissolve and redeposit onto larger particles. Ostwald ripening occurs spontaneously because large particles are more thermodynamically stable than small particles since the internal pressure in a particle is inversely proportional to its radius. This internal pressure difference results from molecules on the surface of a particle being less stable than the more well-ordered particles in the interior of the particle. In addition, large particles have a lower surface-to-volume ratio than smaller particles, which results in a lower, and more stable, energy than small particles in a given distribution. These properties cause smaller particles to dissolve faster than larger particles, and the molecules to deposit from solution onto the larger particles. Over time, the fraction of small particles in solution will decrease while the fraction of large particles in solution increases. Ostwald ripening is a well understood process and the particle growth by Ostwald ripening can be calculated if sufficient variables of the suspension are known (see, for example, van Westen, T. et al., "Effect of temperature cycling on Ostwald ripening", Crystal Growth & Design, Vol. 18, pp. 4952-4962 (2018)).

The present invention improves the stability of low-solubility drug actives and claims actives dispersed in a solvent by physically modifying these ingredients to reduce their particle size to at most 10 μm. The particle size of drug actives and claims actives may be reduced using common comminution methods to reduce the median particle size to at most 10 μm. This reduction in particle size results in ingredients with a size below the threshold of what may perceived on human skin. Reducing the particle size of drug actives and claims actives allows these ingredients to be added to solutions in an amount greater than the amount necessary to saturate the solution. The improved stability may be achieved without the use of additional stabilizing ingredients, such as surfactants or emulsifiers.

Reducing the particle size of drug actives and claims actives in suspension improves their stability by discouraging large particle growth. Ingredients with a very small particle size provide a large number of nucleation sites or seeds for crystallization within a suspension containing the ingredients. Having many nucleation sites allows many particles to grow a small amount rather than allowing fewer particles grow a large amount and develop into larger crystals. Although the ingredients may exhibit particle growth through Ostwald ripening, it has been determined that the rate of formation of particles having a median particle size larger than 10 μm through Ostwald ripening is significantly greater than the typical shelf life of most consumer products containing ingredients in suspension.

Reducing the particle size of drug actives and claims actives in suspension also improves their bioavailability. Typically, ingredients in the solid phase are not considered to be bioavailable. Reducing the particle size of drug actives and claims actives to below 10 μm significantly increases the surface area of these ingredients. The increased surface area of drug actives and claims actives results in these ingredients being bioavailable even when present in the solid phase.

Reducing the particle size of drug actives and claims actives also removes limitations on how these ingredients may be added to formulations. Drug actives and claims actives with reduced particle sizes are present as suspended fine particles in solution, which allows their introduction in the solid phase. The presence of drug actives and claims actives in the solid phase permits their addition to formulation phases in which these ingredients typically have limited solubility. For example, water-compatible ingredients may be added to the oil phase of emulsions as well as lipophilic preparations and even anhydrous preparations. Accordingly, the methods for improving the stability of ingredients in solution may be applied to any type of formulation.

A method of preparing a suspension includes reducing the particle size of a low-solubility ingredient to at most 10 μm and adding the ingredient to a solvent in an amount greater than the saturation limit of the ingredient in the solvent. The ingredient may be added to the solvent followed by reducing the particle size of the ingredient. Alternatively, the particle size of the ingredient may be reduced before adding the ingredient to the solvent.

The suspension may be prepared at ambient temperatures of 15-30° C., including 16° C., 17° C., 18° C., 19° C., 20° C. 21° C., 22° C., 23° C., 24° C., 25° C., 26° C., 27° C., 28° C. and 29° C. Preferably, the suspension is prepared at 25° C.

The low-solubility ingredient may be a drug active, a claims active, or combinations thereof. Preferred ingredients include those having a solubility of at most 1.0% in the solvent at 25° C. More preferred ingredients include those having a solubility of at most 0.5% in the solvent at 25° C. Examples of low-solubility ingredients include allantoin (solubility limit of 0.5% in water at 25° C.), quercetin (very poorly soluble in neutral water), quercetin dihydrate (very poorly soluble in neutral water), rutin (solubility limit of 0.013% in water at 25° C.), multifunctional curcuminoid additives and their derivatives (including curcumin, demethoxycurcumin, bisdemethoxycurcumin and tetrahydrodiferuloyl-methane), phenol antioxidants (including polyphenols such as tannic acid, ellagic acid and raspberry ellagitannin), flavonoids, isoflavonoids such as galbridin, flavanols (including catechins such as epigallocatechin gallate (EGCG)), dimethylmethoxy chromanol, carotenoids (including xanthophylls, astaxanthin, zeaxanthin and lutein) and resveratrol (solubility of 0.03 g/L in water).

The particle size of the ingredient may be reduced using any comminution method that is capable of reducing the particle size to below 10 μm. Preferably, the comminution method is capable of reducing the particle size to below 5 μm. More preferably, the comminution method is capable of reducing the particle size to below 3 μm. Most preferably, the comminution method is capable of reducing the particle size to below 1 μm. A preferred comminution method is milling. Examples of suitable milling devices include vibratory mills, media mills, jet mills and hammer mills.

The comminution is preferably carried out in a liquid carrier that is suitable for use in human topical applications. The liquid carrier may optionally be the solvent. Examples of suitable liquid carriers include humectants such as water, glycerin, propanediol and caprylyl glycol; hydrocarbons such as squalene, isodecane and polyisobutane; alcohols such as ethanol; glycerides such as triglycerides and capric/caprylic triglycerides; cosmetic fluids such as linear alkyl benzoates, C12-C15 alkyl benzoate, ethylhexyl benzoate, isopropyl isostearate, jojoba esters, isoamyl laurate, octyldodecyl neopentanoate, butyloctyl salicylate, tridecyl salicylate and shea butter ethyl esters; vegetable oils and silicones. A preferred aqueous carrier is deionized water. A preferred non-aqueous liquid carrier is C12-C15 alkyl benzoate.

The comminution parameters may be varied to produce a desired final particle size. Variable comminution parameters include the choice of comminution method, duration of comminution, acceleration (for vibratory mills), revolutions per minute (for media mills), type of media, size of media and volume percent of media. Preferred media include 0.3 mm and 0.5 mm diameter yttria-stabilized zirconia media.

The particle size of the ingredient may be reduced to 0.1-9.9 μm, including 0.2 μm, 0.3 μm, 0.4 μm, 0.5 μm, 0.6 μm, 0.7 μm, 0.8 μm, 0.9 μm, 1.0 μm, 1.1 μm, 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, 2.5 μm, 2.6 μm, 2.7 μm, 2.8 μm, 2.9 μm, 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, 5.0 μm, 5.5 μm, 6.0 μm, 6.5 μm, 7.0 μm, 7.5 μm, 8.0 μm, 8.5 μm, 9.0 μm, 9.5 μm, 9.6 μm, 9.7 μm and 9.8 μm. Preferably, the particle size is reduced to at most 5 μm, more preferably the particle size is reduced to at most 3 μm, most preferably the particle size is reduced to at most 1 μm.

A preferred ingredient with a reduced particle size is allantoin having an average particle size of at most 10 μm. Allantoin may have an average particle size of 0.1-9.9 μm, including 0.1-5 μm, 0.1-3 μm and 0.5-3 μm. Preferably, the allantoin has an average particle size of at most 5 μm, at most 3 μm, at most 1 μm or at most 0.5 μm. A suspension may be formed by adding allantoin having an average particle size of at most 10 μm to a solvent.

The size of the particles may be determined using any suitable particle size determination method. Examples of suitable particle size determination include static light scattering, optical microscopy and electron microscopy. Static light scattering may be used to determine the number weighted and volume weighted particle size distributions. Optical microscopy may be used to estimate the particle size by volume or number.

Drug actives and claims actives with reduced particle sizes may be present in compositions in an amount greater than the amount necessary to saturate a solution containing these ingredients. This may be measured by reference to the solubility limit of the ingredient in a given solvent. For example, drug actives and claims actives may be present in a composition at 2-1000 times their solubility limit, including 3, 4, 5, 6, 7, 8, 9, 10, 20, 30, 40, 50, 60, 70, 80, 90, 100, 200, 300, 400, 500, 600, 700, 800 or 900 times their solubility limit.

The suspension of drug actives and/or claims actives may be added to one or more mixtures to create a formulation. The mixture may be a solution, a suspension or a colloid, such as an emulsion, sol, foam or gel. The reduced particle size of the ingredients in suspension allows the solution to be added to any mixture suitable for topical human or animal use. For example, the suspension may be added to the continuous phase of an oil-in-water emulsion, the continuous phase of a water-in-oil emulsion, lipophilic preparations or anhydrous preparations.

A composition may contain a low-solubility ingredient having a particle size of at most 10 μm dispersed in a solvent. The ingredient may be present in an amount greater than the saturation limit of the ingredient in the solvent. The solvent may be any substance that is suitable for topical human or animal use. Preferably, the solvent is a pharmaceutically acceptable solvent. The ingredient may be a drug active, a claims active or combinations thereof.

The stability of the composition may be evaluated by subjecting it to one or more tests that model the long-term stability of compositions. Preferably, the composition passes the freeze-thaw cycling test. More preferably, the composition passes the extended freeze-thaw cycling test. Preferably, the composition passes the shelf stability test. The stability of the composition may also be evaluated by subjecting it to one or more tests developed by an independent organization, such as the International Council for Harmonisation of Technical Requirements for Pharmaceuticals for Human Use (ICH). Preferably, the composition is stable under the ICH accelerated stability conditions.

The composition preferably is suitable for topical human or animal use. The composition may be evaluated to determine its suitability for topical use by applying it to the skin of a human tester. Preferably, the composition passes the skin feel test.

The composition may be formulated for use in a variety of different applications. Examples of suitable formulations include medications (medicines and pharmaceuticals or drugs), baby products (lotions, oils, powders and creams), bath products (oils, tablets, salts, soaps, detergents and bubble baths), eye makeup (eyebrow pencils, eyeliners, eye shadow, eye lotions, eye makeup remover and mascara), fragrance products, hair care products (conditioners, hair sprays/fixatives, straighteners, permanent waves, rinses, shampoos and tonics), makeup/cosmetics (blushes, face powders, foundations, lipsticks, makeup bases and rouges), nail care products (cuticle softeners, creams and lotions), oral hygiene products (dentifrices/toothpastes, mouthwashes and breath fresheners), personal hygiene products (deodorants and douches), shaving products (aftershaves and shaving cream), skin care products (skin cleansing creams, lotions, liquids and pads; face and neck creams, lotions, powders and sprays; body and hand creams, lotions, powders and sprays; foot powders and sprays; moisturizers; night creams, lotions, powders and sprays; paste masks/mud packs; and skin fresheners), sun exposure products (sunscreens; suntan gels, creams, liquids and sprays; indoor tanning preparations) and nutritional supplements (oils, suspensions and other liquids containing vitamins, minerals, proteins, amino acids, bodybuilding supplements, essential fatty acids, natural products or probiotics; nutritional beverages; nutritional oil supplements). Preferred formulations include sunscreens, skin care products and nutritional/dietary supplements.

The composition may be provided in any form suitable for its intended route of administration. For example, a composition intended for topical application may be provided as a topical suspension, lotion, cream, ointment, gel, hydrogel, foam, paste, tincture, liniment, sprayable liquid or aerosol.

The composition may be formulated for human or animal consumption. A consumable composition may contain ingredients such as nutritional supplements or food additives having a particle size of at most 10 μm dispersed in a solvent.

EXAMPLES

Example 1—Comparative Test Between Comminuted Allantoin Suspensions and Aqueous Allantoin Solutions A 10.0 wt % allantoin (DSM, (2,5-dioxo-4-imidazolidi-nyl)urea, CAS No. 97-59-6) suspension was prepared in deionized water. The suspension was milled for 3 minutes on a vibratory mill at an acceleration of 100 G using 0.5 mm diameter yttria-stabilized zirconia media at 50 volume percent. The suspension was examined under an optical microscope and the primary particle size was estimated to be approximately 3 microns (3 μm) by volume and 1 micron (1 μm) by number.

A 1.52 wt % allantoin (DSM, (2,5-dioxo-4-imidazolidinyl)urea, CAS No. 97-59-6) suspension was prepared in deionized water. The suspension was milled for 3 minutes on a vibratory mill at an acceleration of 100 G using 0.5 mm diameter yttria-stabilized zirconia media at 50 volume percent. The suspension was examined under an optical microscope and the primary particle size was estimated to be approximately 3 microns (3 μm) by volume and 1 micron (1 μm) by number.

Comparative solutions were prepared at 10.0 wt % and 1.52 wt % allantoin in deionized water. The comparative solutions were heated to 80° C. under light mixing for approximately 15 minutes. A manufacturer's technical data sheet indicated that stable solutions may be prepared at this temperature with no decomposition. The 1.52 wt % solution achieved complete dissolution, while the 10.0 wt % solution achieved nearly complete dissolution.

Visual Analysis

Figure 2:
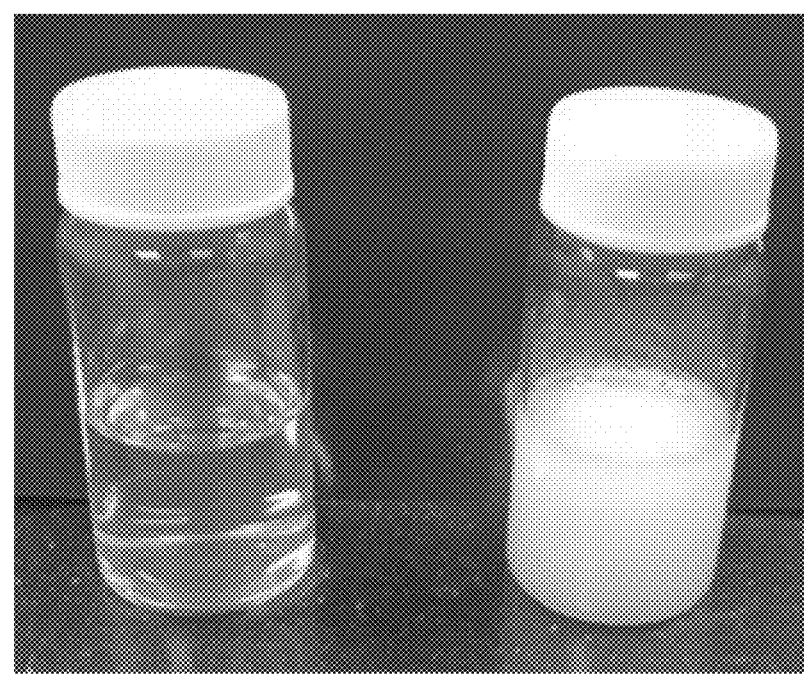
FIG. 2 is a photograph of a 1.52 wt % allantoin suspension prepared by reducing the particle size of allantoin and a 1.52 wt % allantoin solution prepared without reducing the particle size of allantoin.

Photographs of the samples were taken. FIG. 1 is a photograph of the 10.0 wt % allantoin suspension and solution. FIG. 2 is a photograph of the 1.52 wt % allantoin suspension and solution. As may be seen in FIGS. 1 and 2, the milled suspensions appeared opaque and the solutions appeared transparent.

Freeze-Thaw Cycling Test

Figure 3:
FIG. 3 is a photograph of a 10.0 wt % allantoin suspension prepared by reducing the particle size of allantoin and a 10.0 wt % allantoin solution prepared without reducing the particle size of allantoin after one freeze-thaw cycle.
Figure 4:
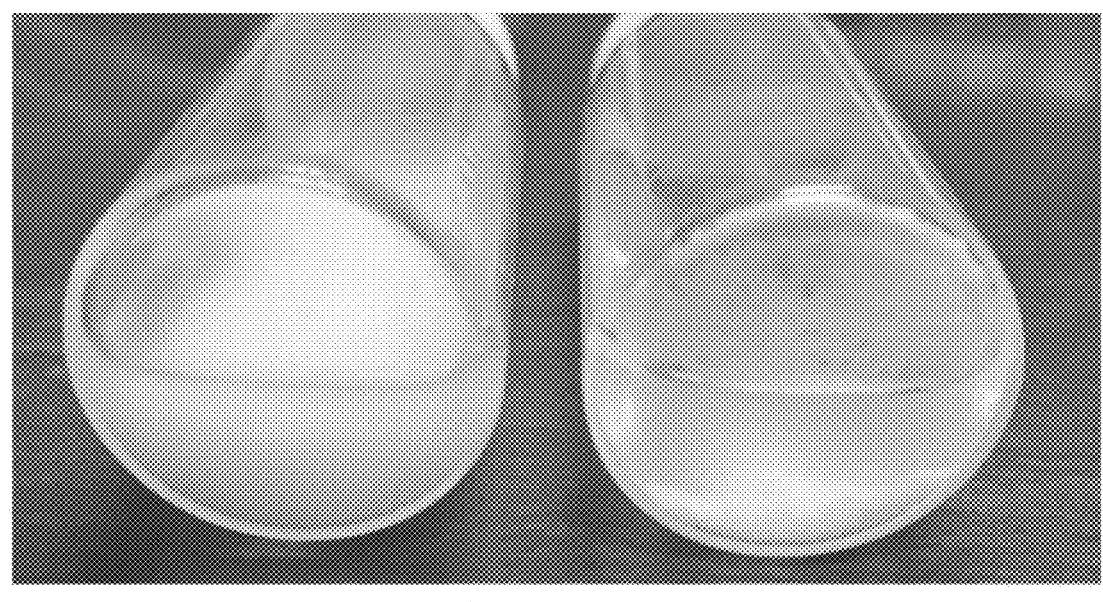
FIG. 4 is a photograph of a 1.52 wt % allantoin suspension prepared by reducing the particle size of allantoin and a 1.52 wt % allantoin solution prepared without reducing the particle size of allantoin after one freeze-thaw cycle.

The samples were tested for freeze-thaw stability and behavior. The suspensions and solutions were placed in a freezer at −20° C. for 6 hours and subsequently returned to room temperature. Photographs of the samples were taken. FIG. 3 is a photograph of the 10.0 wt % allantoin suspension and solution after one freeze-thaw cycle. FIG. 4 is a photograph of the 1.52 wt % allantoin suspension and solution after one freeze-thaw cycle.

The allantoin suspensions remained homogenous after one freeze-thaw cycle and showed no evidence of visible precipitates. By contrast, the allantoin solutions showed a large fraction of precipitation and included significant large crystals that settled out of solution. The crystals were discernable by eye, which indicates that the crystals were likely larger than 30 microns (30 μm). These results were exhibited at both concentrations for the suspensions and the solutions.

Figure 5:
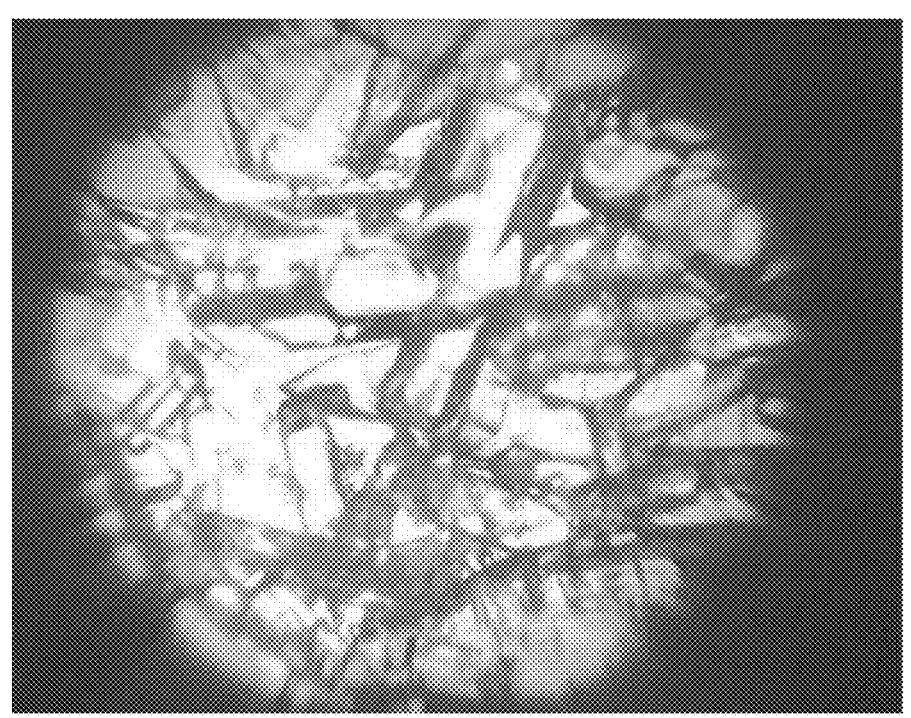
FIG. 5 is an optical microscope image at 40× magnification of a 1.52 wt % allantoin solution prepared without reducing the particle size of allantoin after one freeze-thaw cycle.
Figure 6:
FIG. 6 is an optical microscope image at 200× magnification of a 1.52 wt % allantoin solution prepared without reducing the particle size of allantoin after one freeze-thaw cycle.

The 1.52 wt % allantoin samples were then examined using optical microscopy. FIG. 5 is an optical microscope image at 40× magnification of the 1.52 wt % allantoin solution after one freeze-thaw cycle. FIG. 6 illustrates an optical microscope image at 200× magnification of the 1.52 wt % allantoin solution after one freeze-thaw cycle. FIG. 5 and FIG. 6 both show large crystals. Most of the precipitated crystals were larger than 10 microns (10 μm) in at least one aspect. A substantial number of crystals were larger than 30 microns (30 μm) in at least one aspect. Some particles exceeded the field size at some magnifications, which indicated that these crystals were larger than 100 microns (100 μm) in at least one aspect.

Figure 7:
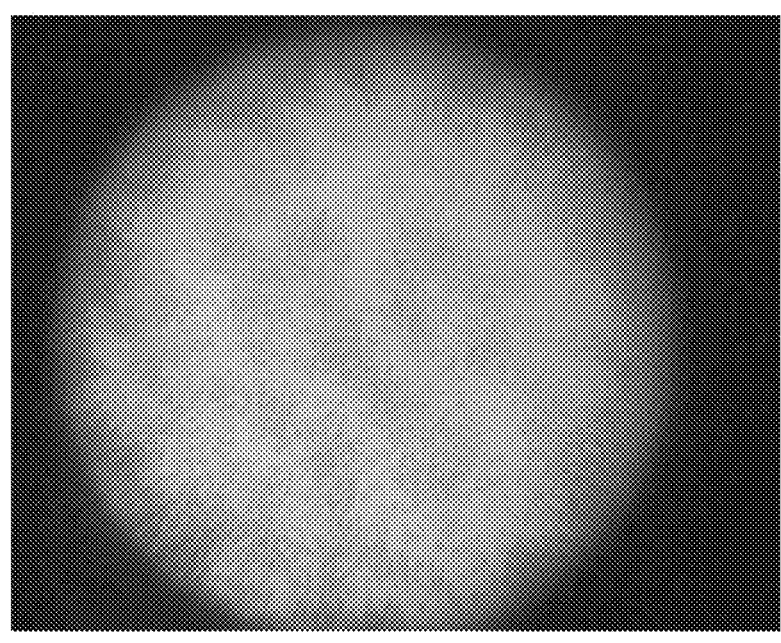
FIG. 7 is an optical microscope image at 40× magnification of a 1.52 wt % allantoin suspension prepared by reducing the particle size of allantoin after one freeze-thaw cycle.
Figure 8:
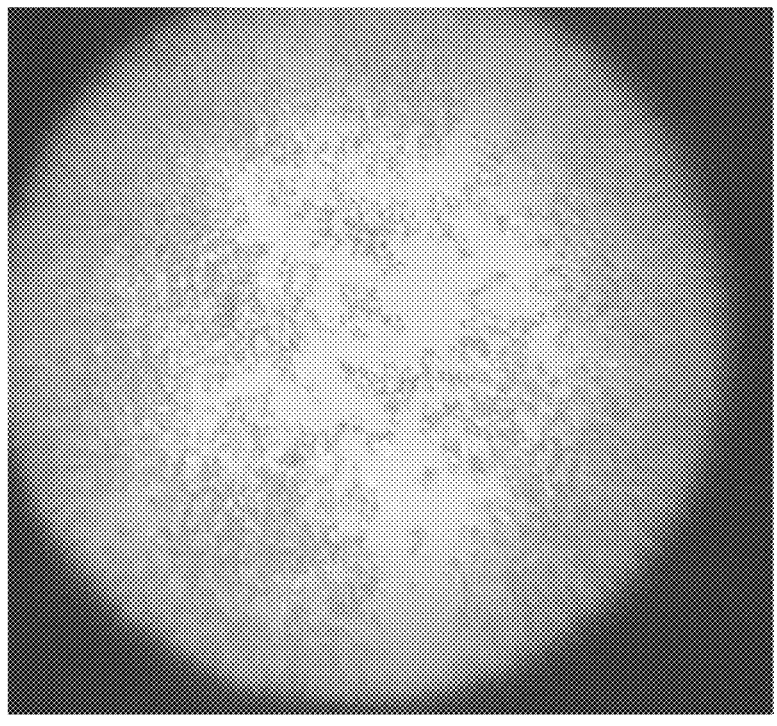
FIG. 8 is an optical microscope image at 200× magnification of a 1.52 wt % allantoin suspension prepared by reducing the particle size of allantoin after one freeze-thaw cycle.

FIG. 7 illustrates an optical microscope image at 40× magnification of the 1.52 wt % allantoin suspension after one freeze-thaw cycle. FIG. 8 illustrates an optical microscope image at 200× magnification of the 1.52 wt % allantoin suspension after one freeze-thaw cycle. FIG. 7 and FIG. 8 show that no large particles were formed as a result of the freeze-thaw cycle. In addition, no discernable particle growth was observed at either magnification. The lack of particle growth indicated that the primary particle size was approximately 3 microns (3 μm) by volume and less than 1 micron (1 μm) by number. The upper limit of the particle size by volume was confirmed to be less than 4 microns (4 μm) by drawing the suspension down on a Hegman grind gauge.

Skin Feel Test

The allantoin suspensions were tested for skin feel. The 1.52 wt % suspension and the 10.0 wt % suspension were applied to the skin after one freeze-thaw cycle. Neither suspension developed crystals of sufficient size to be discerned in a skin feel test. These results were consistent with the particle size determined by optical microscopy. The skin feel test indicated that that the allantoin suspensions were both suitable for cosmetic preparations.

Loss on Drying Test

Two 1.52 wt % allantoin solutions were tested for loss on drying (LOD) at 105° C. after one freeze-thaw cycle and returning to 25° C. The LOD of the clear supernatant indicated an allantoin concentration of 0.25-0.35%. This concentration range was consistent with the initial solubility from the thawing cycle. The concentration was predicted to return to the concentration limit of 0.5% at 25° C. over time. However, the rate of dissolution was predicted to be depressed since the precipitation fraction included large crystals with a low surface area.

Example 2—Repeated Freeze-Thaw Cycling Test for Comminuted Allantoin Suspension

The 1.52 wt % allantoin comminuted suspension described in Example 1 was subject to nine additional freeze-thaw cycles (a total of 10 freeze-thaw cycles). The suspension was then examined using optical microscopy. No discernable particle size growth was observed.

These results indicate that solutions containing an ingredient having a reduced particle size and present at a level above its solubility limit in the solvent are highly stable, and that this high stability can be achieved without the use of stabilizing ingredients.

Example 3—Preparation of 20% Aqueous Allantoin Concentrate Suspension

Figure 9:
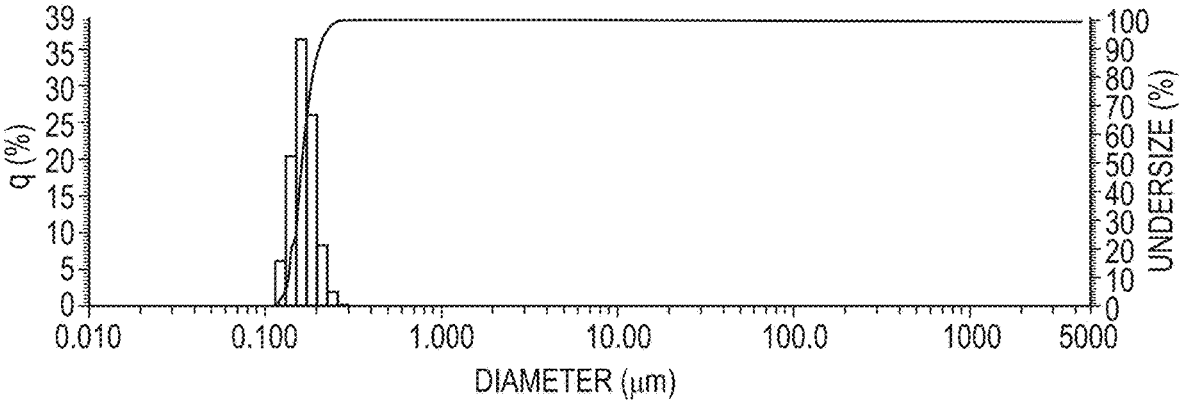
FIG. 9 illustrates the number weighted particle size distribution of a 20.0 wt % allantoin suspension in deionized water prepared by reducing the particle size of allantoin in a 0.25 L media mill at 3000 RPM using 0.3 mm diameter yttria-stabilized zirconia media.
Figure 10:
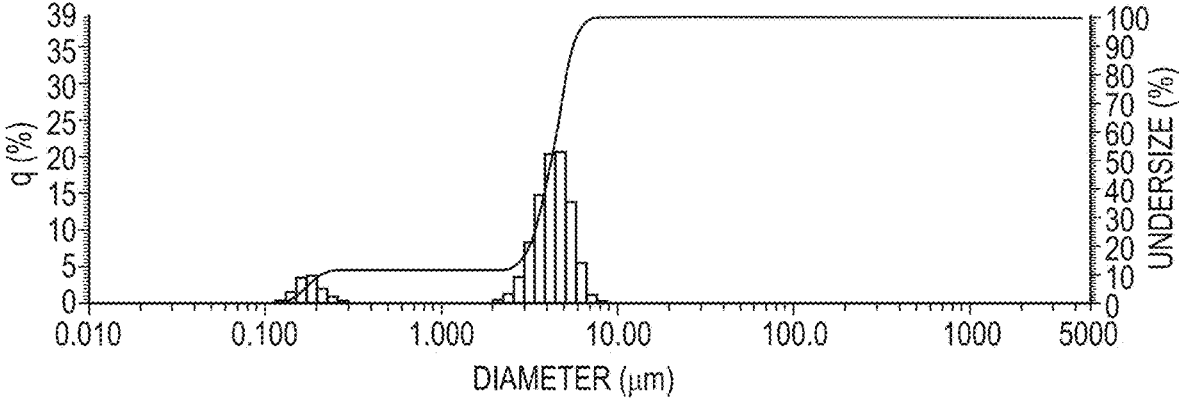
FIG. 10 illustrates the volume weighted particle size distribution of a 20.0 wt % allantoin suspension in deionized water prepared by reducing the particle size of allantoin in a 0.25 L media mill at 3000 RPM using 0.3 mm diameter yttria-stabilized zirconia media.

A 20.0 wt % allantoin (DSM, (2,5-dioxo-4-imidazolidinyl)urea, CAS No. 97-59-6) suspension was prepared in deionized water. The suspension was milled in a 0.25 L media mill at 3000 RPM using 0.3 mm diameter yttria-stabilized zirconia media. The particle size distribution of the resultant suspension showed a number weighted mean particle size of 0.167 microns (0.167 μm) and a volume weighted mean particle size of 3.9 microns (3.9 μm) as measured by static light scattering using a HORIBA® LA-960 laser particle size analyzer. FIG. 9 illustrates the number weighted particle size distribution. FIG. 10 illustrates the volume weighted particle size distribution. Optical microscopy analysis of the suspension indicated a particle size consistent with the comminuted allantoin suspensions described in Example 1.

The 20.0 wt % allantoin suspension was added to the continuous phase of an oil-in-water sunscreen emulsion at a concentration of 0.7% in the water phase. The resulting formulation was shown to be stable under the International Council for Harmonisation of Technical Requirements for Pharmaceuticals for Human Use (ICH) accelerated stability conditions.

These results indicate that aqueous suspensions can contain allantoin at concentrations significantly above its solubility limit when the particle size of allantoin has been reduced to below 10 μm. In addition, the high-concentration suspensions demonstrate high stability in solution.

Example 4—Preparation of 20% Non-Aqueous Allantoin Concentrate Suspension

Figure 11:
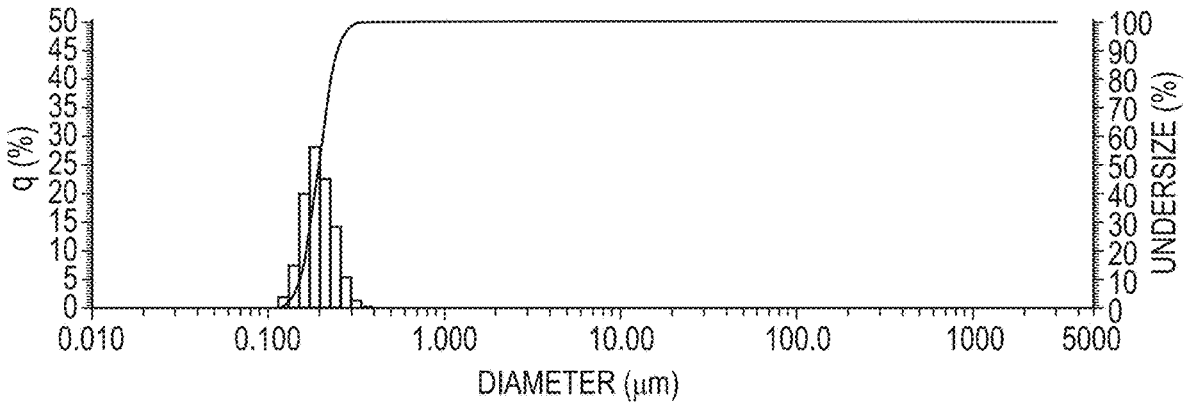
FIG. 11 illustrates the number weighted particle size distribution of a 20.0 wt % allantoin suspension in C12-C15 alkyl benzoate prepared by reducing the particle size of allantoin in a 0.25 L media mill at 3000 RPM using 0.3 mm diameter yttria-stabilized zirconia media.
Figure 12:
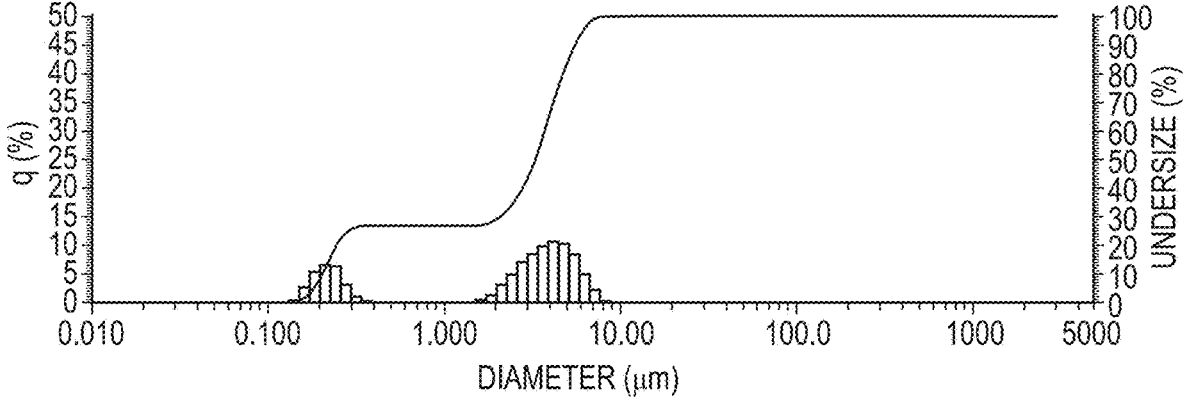
FIG. 12 illustrates the number weighted particle size distribution of a 20.0 wt % allantoin suspension in C12-C15 alkyl benzoate prepared by reducing the particle size of allantoin in a 0.25 L media mill at 3000 RPM using 0.3 mm diameter yttria-stabilized zirconia media.

A 20.0 wt % allantoin (DSM, (2,5-dioxo-4-imidazolidi-nyl)urea, CAS No. 97-59-6) suspension was prepared in C12-C15 alkyl benzoate (FINSOLV® TN, Innospec). The suspension was milled in a 0.25 L media mill at 3000 RPM using 0.3 mm diameter yttria-stabilized zirconia media. The particle size distribution of the resultant suspension showed a number weighted mean particle size of 0.195 microns (0.195 μm) and a volume weighted mean particle size of 3.0 microns (3.0 μm) as measured by static light scattering using a HORIBA® LA-960 laser particle size analyzer. FIG. 11 illustrates the number weighted particle size distribution. FIG. 12 illustrates the volume weighted particle size distribution. Optical microscopy analysis of the suspension indicated a particle size consistent with the comminuted allantoin suspensions described in Example 1.

The 20.0 wt % allantoin suspension was added to the continuous phase of a water-in-oil sunscreen emulsion at a concentration of 0.7% in the water phase. The resulting formulation was shown to be stable under the International Council for Harmonisation of Technical Requirements for Pharmaceuticals for Human Use (ICH) accelerated stability conditions.

These results indicate that non-aqueous suspensions can contain allantoin at concentrations significantly above its solubility limit when the particle size of allantoin has been reduced to below 10 μm. In addition, the high-concentration suspensions demonstrate high stability in solution.

Example 5—Bioavailability Study

A comminuted suspension of allantoin in deionized water and a comparative solution of allantoin in deionized water (not comminuted) were prepared as described in Example 1. Sunscreens were then prepared containing the comminuted allantoin suspension and zinc oxide, and containing the allantoin solution and zinc oxide.

A human subject applied each sunscreen to separate areas of their skin. Their skin was then exposed to ultraviolet light. The area of skin that received the sunscreen with the comminuted allantoin suspension exhibited less erythema (redness) than the area of skin that received the sunscreen containing the allantoin solution. These results indicate that reducing the particle size of the allantoin by comminution increased the bioavailability of the allantoin.

REFERENCES

1. Igile, G. O. et al., "Rapid method for the identification and quantification of allantoin in body creams and lotions for regulatory activities", International Journal of Current Microbiology and Applied Sciences, Vol. 3, No. 7, pp. 552-557 (2014).
2. Becker, L. C. et al., "Final report of the safety assessment of allantoin and its related complexes", International Journal of Toxicology, Vol. 29. Supplement 2, pp. 84S-97S (2010).
3. van Westen, T. et al., "Effect of temperature cycling on Ostwald ripening", Crystal Growth & Design, Vol. 18, pp. 4952-4962 (2018).

What is claimed is:

1. A composition, comprising a low-solubility ingredient having a particle size of at most 10 μm dispersed in a solvent,
    wherein the ingredient is present in an amount greater than the saturation limit of the ingredient in the solvent,
    the composition passes the freeze-thaw cycling test, and
    the composition is anhydrous.

2. The composition of claim 1, wherein the composition passes the extended freeze-thaw cycling test.

3. The composition of claim 1, wherein the composition passes the skin feel test.

4. The composition of claim 1, wherein the ingredient is selected from the group consisting of drug actives, claims actives and combinations thereof.

5. The composition of claim 1, wherein the ingredient has a particle size of at most 1 μm by number as measured by static light scattering.

6. The composition of claim 1, wherein the ingredient comprises at least one substance selected from the group consisting of quercetin, quercetin dihydrate, rutin, multifunctional curcuminoid additives and their derivatives, curcumin, demethoxycurcumin, bisdemethoxycurcumin, tetrahydrodiferuloyl-methane, phenol antioxidants, tannic acid, ellagic acid, raspberry ellagitannin, flavonoids, isoflavonoids, galbridin, flavanols, catechins, epigallocatechin gallate (EGCG), dimethylmethoxy chromanol, carotenoids, xanthophylls, astaxanthin, zeaxanthin, lutein, and resveratrol.

7. The composition of claim 1, wherein the solvent is selected from the group consisting of humectants, hydrocarbons, alcohols, glycerides, cosmetic fluids, vegetable oils, and silicones.

8. The composition of claim 1, wherein the composition is formulated as a topical solution, lotion, cream, ointment, gel, hydrogel, foam, paste, tincture, liniment, sprayable liquid or aerosol.

9. The composition of claim 1, wherein the composition comprises a formulation selected from the group consisting of medications, baby products, bath products, fragrance products, hair care products, cosmetics, nail care products, oral hygiene products, personal hygiene products, shaving products, skin care products, sun exposure products and nutritional supplements.

10. The composition of claim 1, wherein the composition comprises a sunscreen.

11. The composition of claim 1, wherein the composition is a skin care product.

12. The composition of claim 1, wherein the ingredient comprises a nutritional supplement or a food additive.

13. The composition of claim 1, wherein the ingredient comprises tetrahydrodiferuloyl-methane.

14. The composition of claim 1, wherein the ingredient has a particle size of 0.1 to 1.0 μm by number as measured by static light scattering.

15. The composition of claim 1, wherein the ingredient has a particle size of 0.1 to 0.5 μm by number as measured by static light scattering.

16. The composition of claim 1, wherein the ingredient has a particle size of 0.1 to 0.2 μm by number as measured by static light scattering.

17. The composition of claim 1, wherein the ingredient comprises at least one substance selected from the group consisting of quercetin, quercetin dihydrate, rutin, demethoxycurcumin, bisdemethoxycurcumin, tetrahydrod-iferuloyl-methane, phenol antioxidants, tannic acid, ellagic acid, raspberry ellagitannin, flavonoids, isoflavonoids, gal-bridin, flavanols, catechins, epigallocatechin gallate (EGCG), dimethylmethoxy chromanol, carotenoids, xantho-phylls, astaxanthin, zeaxanthin, lutein, and resveratrol.

18. A composition, comprising:
tetrahydrodiferuloyl-methane having a particle size of 0.1 to 1 μm by number as measured by static light scatter-ing, dispersed in a solvent,
wherein the tetrahydrodiferuloyl-methane is present in an amount greater than the saturation limit of the tetrahy-drodiferuloyl-methane in the solvent,
the composition passes the freeze-thaw cycling test, the extended freeze-thaw cycling test, and the skin feel test,
the composition is anhydrous, and
the solvent is selected from the group consisting of humectants, hydrocarbons, alcohols, glycerides, cos-metic fluids, vegetable oils, and silicones.

19. The composition of claim 18, wherein the composi-tion comprises a sunscreen.

20. The composition of claim 18, wherein the tetrahy-drodiferuloyl-methane has a particle size of 0.1 to 0.2 μm by number as measured by static light scattering.

* * * * *